United States Patent [19]

Schakenraad et al.

[11] Patent Number: 5,679,460
[45] Date of Patent: Oct. 21, 1997

[54] METHOD FOR MODIFYING FLUORINE-CONTAINING PLASTIC, MODIFIED PLASTIC AND BIO-MATERIAL CONTAINING THIS PLASTIC

[75] Inventors: Josephus Maria Schakenraad, Haren; Hendrik Jan Busscher, Thesinge, both of Netherlands

[73] Assignee: Rijksuniversiteit Groningen, Netherlands

[21] Appl. No.: 137,055
[22] PCT Filed: Apr. 13, 1992
[86] PCT No.: PCT/NL92/00069
§ 371 Date: Mar. 15, 1994
§ 102(e) Date: Mar. 15, 1994
[87] PCT Pub. No.: WO92/18320
PCT Pub. Date: Oct. 29, 1992

[30] Foreign Application Priority Data

Apr. 15, 1991 [NL] Netherlands .................... 91.00654
Dec. 17, 1991 [NL] Netherlands .................... 91.02107

[51] Int. Cl.⁶ .................... B29C 59/16; B29C 59/10; B32B 27/30
[52] U.S. Cl. .................... 428/421; 134/1.1; 216/50; 216/65; 216/66; 216/67; 428/422
[58] Field of Search .................... 428/421, 422; 216/50, 65, 66, 67; 134/1.1

[56] References Cited

U.S. PATENT DOCUMENTS

| | | | |
|---|---|---|---|
| 4,199,650 | 4/1980 | Mirtich et al. | 428/421 |
| 4,632,842 | 12/1986 | Karwoski et al. | 427/2 |
| 5,437,900 | 8/1995 | Kuzowski | 428/36.1 |

OTHER PUBLICATIONS

H. Griesser, "Long Term Behaviour of Contact Angles on Modified Fluorocarbon Surfaces," *Polym. Mater. Sci. Eng.*, vol. 62, 1990, pp. 872–875.

G. Picha, "Tissue Response to Peritoneal Implants," *Chemical Abstracts*, vol. 94, No. 18, 1980.

*Primary Examiner*—D. S. Nakarani
*Attorney, Agent, or Firm*—Webb Ziesenheim Bruening Logsdon Orkin & Hanson, P.C.

[57] ABSTRACT

The invention relates to a method for modifying at least a part of the surface of a fluorine-containing plastic, which comprises making the surface hydrophobic by 1) ion-etching the plastic surface; and 2) subsequently treating the plastic surface with flow discharging. The invention also relates to a fluorine-containing plastic having a surface which is at least partially hydrophobe-modified by ion-etching followed by glow discharging, and to materials, such as bio-materials, in which the plastic is incorporated.

18 Claims, 4 Drawing Sheets

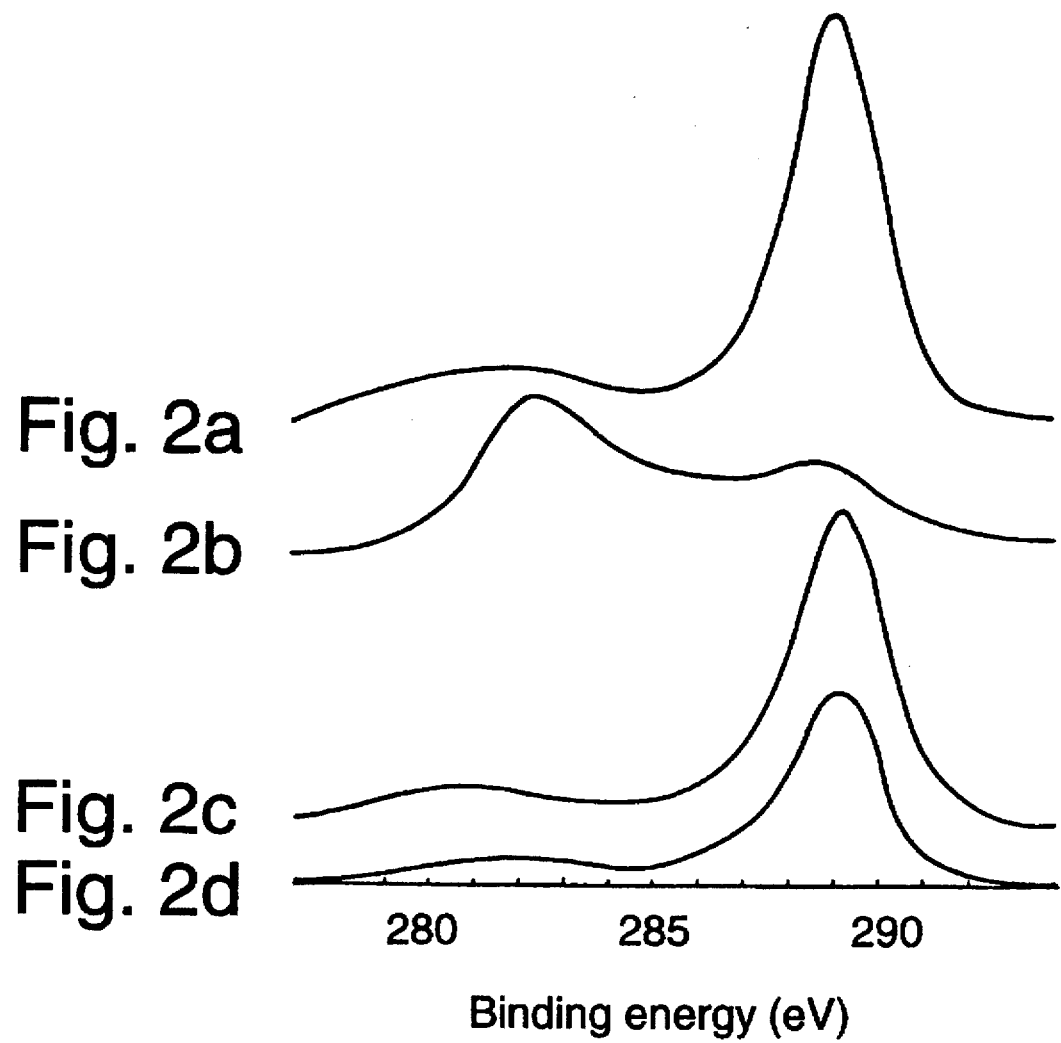

METHOD FOR MODIFYING FLUORINE-CONTAINING PLASTIC, MODIFIED PLASTIC AND BIO-MATERIAL CONTAINING THIS PLASTIC

BACKGROUND OF THE INVENTION

The present invention relates to the modifying of a fluorine-containing plastic, to the modified fluorine-containing plastic and to materials, particularly bio-materials, containing such a modified, fluorine-containing plastic, possibly as coating (plasmapolymers). The invention relates particularly to a method with which the surface of the fluorine-containing plastic can be made superhydrophobic, and according to a preferred embodiment the fluorine-containing plastic is modified such that a portion of the surface becomes superhydrophobic and another portion of the surface hydrophilic. In preference both types of surface are located on either side of a fluorine-containing plastic sheet.

Fluorine-containing plastics, such as polytetrafluoroethylene (PTFE) offer interesting technical applications because of the material properties such as a high thermal and chemical resistance and the hydrophobic nature of the surface. The materials seem very suitable as bio-material. PTFE is for example strong, flexible and bio-inert and can be made elastic and if necessary porous (e-PTFE). This hydrophobic material can be used as bio-material when a small adhesion to body tissues is required, for example at the lumen side of vascular prostheses, paradontological membranes and the visceral side of abdominal wall patches. If a good interaction with body tissue is necessary, as for instance on the dermal side of abdominal wall patches, the use of hydrophilic PTFE is preferred.

SUMMARY OF THE INVENTION

The invention has for its object to modify the surface of fluorine-containing plastics such that the applicability in industrial products and in bio-materials is thereby increased, particularly in that the hydrophobic character of the surface is greatly influenced. This is achieved according to the invention with a method for modifying at least a part of the surface of a fluorine-containing plastic, which method comprises making the surface hydrophobic by:
i) ion-etching the plastic surface; and
ii) subsequently cleaning the treated plastic surface.

DESCRIPTION OF THE PREFERRED EMBODIMENTS

It has been found that due to the combined treatment consisting of ion-etching and glow discharging the hydrophobic character of the fluorine-containing plastic is greatly enlarged. If as a measure of the hydrophobic character the mean contact angle of water on the modified surface is used, the method according to the invention results in an increase of the average contact angle of 108° to more than 125°, preferably more than 130° and even to more than 140°. It is noted that ion-etching alone results in a smaller increase in the hydrophobic character (mean contact angle of water approximately 120°) and that glow discharging alone results in a lessening of the hydrophobic character (mean contact angle of water 100°).

Ion-etching is a per se conventional treatment technique well known to a person skilled in the art.

The cleaning treatment which must be performed on the plastic surface treated by ion-etching after the ion-etching has for its object to remove from the plastic surface substances or structures generated on the plastic surface by the ion-etching. This cleaning treatment can comprise a chemical, physical and/or physical-chemical treatment of the plastic surface treated by ion-etching such as a treatment with acid, base, salts, solvents and/or combinations thereof, assuming that the effect according to the present invention is thereby not adversely affected to any great extent. A cleaning treatment preferred at this moment comprises glow discharging, which is a per se conventional treatment technique.

Suitable for use as fluorine-containing plastic in the modification method according to the invention are those plastics whose mechanical properties are such that the ion-etching and the glow discharging treatment, while optionally the plastic is cooled, does not result in a serious deterioration in the physical and chemical properties of the plastic. In general can be used fluorine- and fluorochlorine-containing plastics such as the polymers polyfluoroethenepropylene (FEP), polytetrafluoroethylene (PTFE), polychlorotrifluoroethylene (PCTFE), polyvinyl fluoride (PVF), polyvinylidene fluoride (PVDF) and copolymers thereof with ($C_2$–$C_6$) alkylene, fluorinated ($C_2$–$C_6$) alkylene such as hexafluoropropylene, fluorinated ($C_1$–$C_6$) alkylvinylether such as perfluoropropylvinylether. Preferred plastics are FEP and PTFE.

As a consequence of the modification method according to the invention the chemical composition of the hydrophobicly modified surface layer is also altered. The hydrophobicly modified surface has an oxygen-carbon concentration ratio (O/C) of generally 0.100–0.200, preferably 0.120–0.180 and a fluorine-carbon concentration ratio (F/C) of generally 1.00–2.000, preferably 1.400–1.800 (measured with XPS).

As a result of the pronounced hydrophobic character of the surface modified according to the invention, these modified plastics can be used on surfaces where adhesion of for instance cells, micro-organisms, proteins and other particles or organisms is undesired, such as in heat exchangers employed in the food industry, on ship hulls and other surfaces coming into contact with water over long periods. As bio-material the modified plastic according to the invention can be used in clinical and dental situations where the adhesion and/or spread of cells and/or micro-organisms is undesirable, such as on the inside of vascular prostheses, heart valves, the visceral side of reconstruction materials for the abdominal wall and with vocal assist devices in the case of a tracheal-oesophageal shunt. In the case of these bio-materials it can be advantageous that there is also a surface present which lends itself to cell adhesion and cell spreading (the outside of vascular prostheses and the dermal side of abdominal wall reconstruction materials). According to the invention another portion of the surface of the fluorine-containing plastic is hydrophilicly modified in accordance with a specific embodiment by:

i) ion-etching the other portion of the plastic surface; and
ii) placing the surface in contact with water.

This hydrophilicly modified surface has a contact angle with water on the modified surface of 6°±5°.

Mentioned and other features of the modification method according to the invention and the fluorine-containing plastics modified according to the invention and their applications will be further elucidated hereinbelow with reference to a number of non-limitative examples.

EXAMPLE 1

FEP-Teflon was obtained from Fluorplast B.V. (Raamsdonkveer, The Netherlands), cut into pieces of 1×2 cm and thoroughly cleaned with acetone and dried.

The samples were subjected to ion-etching making use of a so-called Ion Tech saddle field ion source (Teddington, England) at an argon pressure of $1\times10^{-6}$ to $1\times10^{-4}$ torr, while the ion energy was varied from 5–10 kV. Depending on the argon pressure the ion source flow varied between 8–10 mA. If a fixed sample holder was used the radiating time varied between 5 and 120 minutes, and preferably between 10 and 60 minutes. With the use of a rotating target holder the radiating time amounted to 1–10 hours, and preferably 2–7 hours, for example 5 hours.

After ion-etching the samples were treated with oxygen glow discharging in a PLASMOD (Tegal Corporation, Richmond, Calif.), an inductively coupled instrument (13.56 MHz) with a cylindrical reaction chamber made of quartz (internal diameter 8 cm, length 15 cm). The glow discharging was performed under an oxygen pressure of 15 mbar and at a power of 50W. The glow discharging treatment lasted 0.5 to 10 minutes, and in general 1 to 5 minutes.

In the case of a number of samples, another portion of the surface was hydrophilicly modified by ion-etching of this portion of the surface followed by water contact. Making use for instance of a rotating target holder with an ion bundle treatment at 6 mA, 6 kV and an argon pressure of $4\times10^{-4}$ torr for about 45 minutes. The samples were subsequently stored in water for 24 hours.

The contact angle of the various samples with a number of liquids, namely water, formamide, diiodomethane and α-bromonaphthalene, was measured using a SUPCON EC90 (accuracy 0.5°). The results are shown in table 1.

Using X-ray photoelectron spectroscopy (XPS) the surface concentration ratios for a number of elements were measured on the basis of the $C_{16}$, $O_{1m}$, and $F_{1s}$ peaks and the concentration ratios relative to carbon were calculated using the Wagner sensitivity factors. The results are shown in table 2.

Using infrared spectroscopy it could be demonstrated that the chemical effects of the modification treatment according to the invention are limited to the outer surface of the plastic.

The stylus surface roughness $R_A$ of the diverse samples was calculated from 4.8 mm tracings taken with a perthometer C5D equipped with a 5 μm stylus (opening angle 90°). Ten tracings were recorded and averaged for each sample. The results are shown in table 3.

Using a scanning electron microscope (SEM) micrographs were made at two magnifications after ion-etching and/or oxygen glow discharging.

In the figures:

FIG. 2A shows XPS spectra of untreated FEP-teflon;

FIG. 2B shows XPS spectra of 45 min. ion-etching (8 mA/6 kV/$4\times10^{-4}$ torr argon pressure);

FIG. 2C shows XPS spectra of 5 min. glow discharging (15 mbar oxygen pressure/50W);

FIG. 2D shows XPS spectra of 10 min. ion-etching (8 mA/6 kV/$4\times10^{-4}$ torr argon pressure) followed by 5 min. glow discharging (15 mbar oxygen pressure/50W).

Figure 1A:
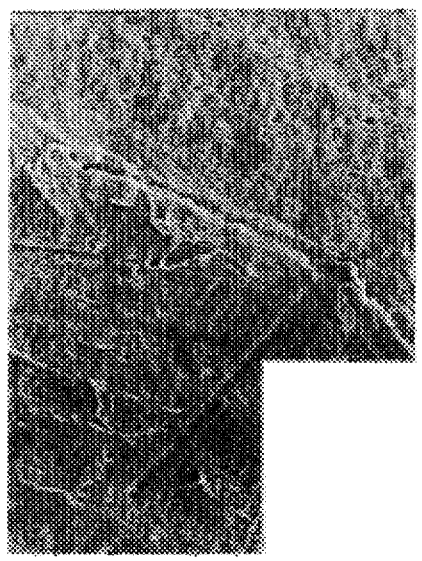
FIG. 1A is untreated
Figures 1, 1A:
Figure 1B:
FIG. 1B is 1 min. glow discharging (15 mbar oxygen pressure/50W)
Figures 1, 1B:
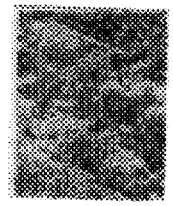
Figure 1C:
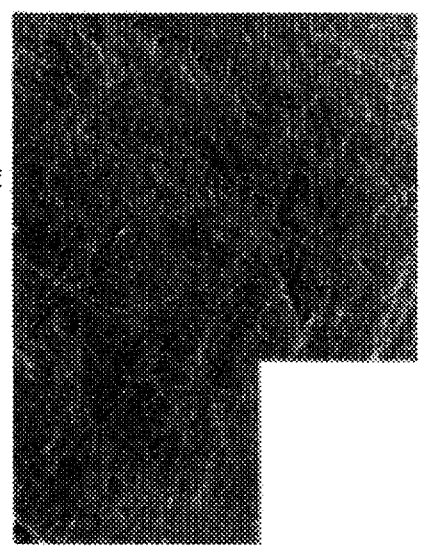
FIG. 1C is 5 min. glow discharging (15 mbar oxygen pressure/50W)
Figures 1, 1C:
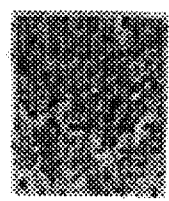

The FIGS. 1A–C show that the glow discharging treatment as such does not affect the topography of the surface. It can be seen from FIGS. 1D–F that a typical micro-surface roughness results after ion-etching formed by stalk-like projections with a diameter generally of 20–60 nm, for example approximately 40 nm, and a length generally of several hundred nanometers, which cover the whole suffice homogeneously. Glow discharging of these surfaces results in a melting down of the upper portions of these projections, and cleaning of intermediate regions, as can be seen in FIGS. 1G–I.

FIG. 2B shows that ion-etching leads to the generation of substances and/or structures with an average binding energy of approximately 282–283 eV. These substances and/or structures are not generated during glow discharging (FIG. 2C) but are removed by the cleaning treatment, such as glow discharging (FIG. 2D).

EXAMPLE 2

The effect of the hydrophobic modification according to the invention on the adhesion and spreading of cells was studied using human fibroblasts. For comparison the same tests were performed using conventional tissue culture polystyrene (TCPS), normal FEP (FEP) and hydrophilicly modified FEP.

Human skin fibroblasts were cultured in RPMI 1640 medium (Gibco) with 15% foetal calf serum (Gibco) and 100 μ/ml of penicillin/streptomycin (Gibco) at 37° C. in air with 5% $CO_2$. Every other day the cells were sub-divided by trypsination (0.15 w/w % 1:250 trypsin) in calcium- and magnesium-free Hanks balance salt solution.

After trypsination $10^4$ cells per $cm^2$ were set out on Greiner plates. The different substrata (n=6) were positioned on the bottom. After 120 minutes photos were taken of the cells and the number of adhered cells per $cm^2$33 $10^4$ (cell density), the mean cell spreading area (MCSA) in $μm^2$ and the spreading area distribution (SEM) were determined per material by morphometric image analysis—(Cambridge Instruments, Quantimet 520). The experiment was performed in triplicate. The results are shown in table 4.

EXAMPLE 3

An elastic vascular prosthesis of e-PTFE (Gore-Tex from W. L. Gore & Associates Inc, Flagstaff, USA) with a length of 1 cm, an internal diameter of 1.55 mm and a pore size of 30 μm was cut open longitudinally, whereafter the luminal surface was hydrophobicly modified according to the invention in the same manner as described in example 1. After the hydrophobic treatment according to the invention the vascular prosthesis was closed with a continuous stitch (Ethylon 9-0, BV-4 needle, Ethicon).

A rabbit (New Zealand White) was anaesthetized with Nembutal (0.5 ml/kg), after which the neck was shaved. Oxygen/nitrous oxide was then used as anaesthetic. Painkilling was carried out using Temgesic, 0.1 ml.

The left-hand arteria carotis was exposed over a length of about 2 cm. After arranging two clamps, 1 cm of the arteria carotis was removed and replaced by the luminal vascular prosthesis hydrophobicly modified according to the invention which was joined at both ends to the arteria carotis using eight stitches (Ethylon 9-0, BV-4 needle, Ethicon).

After the clamps were removed, it was checked and confirmed after 10 minutes and after two hours that blood could pass through the prosthesis. The wound was then closed and the rabbit returned to its hutch. Standard rabbit food and water were provided ad libitum.

One week later the prosthesis was once again exposed under the same standard anaesthetic as described above and it was determined that blood was still passing through the prosthesis. Before removing the prosthesis heparin was administered to the rabbit in order to avoid coagulation in the removed prosthesis.

Although no cleaning treatment other than glow discharging is described in the examples, it will be apparent that any cleaning treatment is suitable insofar as substances and/or structures are removed (FIG. 2B) with a binding energy of about 282–283 eV and the modified hydrophobic character of the plastic surface is substantially not adversely affected.

TABLE 1

Contact angle (°) after ion-etching (IE) and/or oxygen (15 mbar) glow discharge (Gld, 50 W) for modified PEP-Teflon. ± indicates the standard deviation for three separately manufactured samples.

| treatment duration | water | formamide | diiodo- methane | α-bromo naphtha- lene |
|---|---|---|---|---|
| untreated | 109 ± 2 | 90 ± 4 | 77 ± 3 | 73 ± 1 |
| Modified | | | | |
| IE$^{a)}$, 10 min | 121 ± 4 | 98 ± 16 | 87 ± 14 | 41 ± 14 |
| IE$^{a)}$, 30 min | 120 ± 6 | 102 ± 16 | 95 ± 9 | 75 ± 16 |
| IE$^{a)}$, 60 min | 118 ± 10 | 80 ± 21 | 81 ± 11 | 51 ± 10 |
| Modified | | | | |
| Gld, 1 min | 104 ± 7 | 87 ± 6 | 74 ± 6 | 69 ± 5 |
| Gld, 3 min | 99 ± 6 | 77 ± 9 | 73 ± 5 | 71 ± 3 |
| Gld, 5 min | 99 ± 7 | 80 ± 7 | 69 ± 4 | 69 ± 4 |
| Hydrophobicly-modified according to the invention | | | | |
| IE$^{a)}$, 10 min + Gld, 5 min | 131 ± 7 | 110 ± 7 | 96 ± 10 | 85 ± 13 |
| IE$^{a)}$, 30 min + Gld, 5 min | >140$^{c)}$ | 123 ± 3 | 111 ± 5 | 97 ± 14 |
| IE$^{b)}$, 30 min + Gld, 5 min | >140$^{c)}$ | 122 ± 7 | 110 ± 10 | 107 ± 20 |
| Hydrophobicly modified | | | | |
| IE, 45 min/ water contact | 6 | 10 | 26 | 16 |

$^{a)}$IE; 8 mA, 6 kV and 4 × 10$^{-4}$ torr argon pressure
$^{b)}$IE; 10 mA, 10 kV and 2 × 10$^{-4}$ torr argon pressure
$^{c)}$drops did not remain on the surface, angles determined between 140 and 150° (possibly higher)

TABLE 2

Surface concentration ratios measured with XPS after ion-etching (IE) (8 mA, 6 kV and 4 × 10$^{-4}$ argon pressure) and/or oxygen glow discharging (15 mbar oxygen pressure at 50 W for 5 minutes) of FEP-Teflon surfaces.

| IE | Gld | O/C | F/C |
|---|---|---|---|
| no | no | 0.018 | 1.931 |
| 10 min | no | 0.208 | 0.629 |
| 45 min | no | 0.142 | 1.059 |
| 60 min | no | 0.097 | 0.670 |
| no | yes | 0.016 | 1.757 |
| 10 min | yes | 0.133 | 1.511 |
| 30 min | yes | 0.173 | 1.526 |
| 45 min | yes | 0.169 | 1.745 |

TABLE 3

Stylus surface roughness $R_A$ after ion-etching (8 mA, 6 kV and 4 × 10$^{-4}$ torr argon pressure) and/or after oxygen glow discharging (15 mbar oxygen pressure at 50 W) of FEP-Teflon surfaces. ± indicates the standard deviation over ten tracings.

| IE | Gld | $R_A$ [μm] |
|---|---|---|
| no | no | 0.44 ± 0.22 |
| 10 min | no | 0.54 ± 0.07 |
| 60 min | no | 0.74 ± 0.07 |
| no | 5 min | 0.48 ± 0.09 |
| 45 min | 10 min | 0.49 ± 0.04 |
| 45 min | 30 min | 0.35 ± 0.02 |

TABLE 4

Spreading of human skin fibroblasts. A total of 400 cells were measured per material. The standard deviation of the standard error of the mean (SEM) of the mean cell spreading area MCSA is given in %.

| Material | TCPS | FEP | FEP hydrophobicly modified according to the invention | FEP hydrophobicly modified |
|---|---|---|---|---|
| Cell density | 4.5 | 2.8 | 2.8 | 2.3 |
| MCSA | 270 | 209 | 158 | 257 |
| SEN | 6 | 6 | 14 | 9 |
| Significance (a) | # | * | *# | # |

(a):
*indicates a significant difference relative to TCPS, p < 0.01, student t-test;
indicates a significant difference relative to FEP

We claim:
1. Method for modifying at least a part of the surface of a fluorine-containing plastic, which comprises making the surface hydrophobic to the extent wherein the average contact angle of water on the surface is more than 125° by:
 i) ion-etching the plastic surface; and
 ii) subsequently removing substances from the treated plastic surface generated by the ion-etching by means of glow discharging.

2. Method as claimed in claim 1, wherein the fluorine-containing plastic is selected from the group consisting of polyfluoroethenepropylene, polytetrafluoroethylene, polychlorotrifluoroethylene, polyvinyl fluoride, polyvinylidene fluoride and copolymers thereof with $C_{2-6}$ alkylene, fluorinated $C_{2-4}$ alkylene, or fluorinated $C_{1-6}$ alkylvinylether.

3. Method as claimed in claim 2, wherein the fluorine-containing polymer is polyfluoroethenepropylene or polytetrafluoroethylene.

4. Method as claimed in claim 1, wherein the hydrophobicly modified surface has;
 an oxygen-carbon concentration ratio (O/C) of 0.100–0.200; and
 a fluorine-carbon concentration ratio (F/C) of 1.000–2.000.

5. Method as claimed in claim 4, wherein
 the oxygen to carbon ratio is 0.120–0.180 and
 the fluorine to carbon ratio is 1.400–1.800.

6. Method as claimed in claim 1, wherein a modified surface is provided with elongated projections with a diameter in the range of 20–60 nm, wherein the free ends of said elongated projections are melted down.

7. Method as claimed in claim 1, wherein another portion of the surface of the fluorine-containing plastic is hydrophilicly modified by:

i) ion-etching the other portion of the plastic surface; and ii) placing the surface in contact with water.

8. Method as claimed in claim 7, wherein the contact angle of water on the hydrophilicly modified surface amounts to 6°±5°.

9. Plastic as claimed in claim 1, wherein the fluorine-containing plastic is selected from the group consisting of polyfluoroethenepropylene, polytetrafluoroethylene, polychlorotrifluoroethylene, polyvinyl fluoride, polyvinylidene fluoride and copolymers thereof with $C_{2-6}$ alkylene, fluorinated $C_{2-4}$ alkylene, or fluorinated $C_{1-6}$ alkylvinylether.

10. Plastic as claimed in claim 9, wherein the fluorine-containing polymer is polyfluoroethenepropylene or polytetrafluoroethylene.

11. Fluorine-containing plastic, a surface of which is at least partially hydrophobicly modified by ion-etching followed by a cleaning treatment comprising glow discharging.

12. Plastic as claimed in claim 11, wherein the mean contact angle of water on the hydrophobicly modified surface amounts to more than 125°.

13. Plastic as claimed in claim 11, wherein the mean contact angle of water on the hydrophobicly modified surface amounts to more than 130°.

14. Plastic as claimed in claim 11, wherein the hydrophobicly modified surface has;

an oxygen-carbon concentration ratio (O/C) of 0.100–0.200; and a fluorine-carbon concentration ratio (F/C) of 1.000–2.000.

15. Plastic as claimed in claim 11, wherein the oxygen to carbon ratio is 0.120–0.180 and the fluorine to carbon ratio is 1.400–1.800.

16. Plastic as claimed in claim 11, wherein the hydrophobicly modified surface is provided with elongated projections with a diameter in the range of 20–60 nm, free ends whereof are melted down.

17. Plastic as claimed in claim 11, wherein another portion of the surface is hydrophilicly modified.

18. Plastic as claimed in claim 17, wherein the surface is hydrophilicly modified by ion-etching followed by water contact.

* * * * *

UNITED STATES PATENT AND TRADEMARK OFFICE
CERTIFICATE OF CORRECTION

PATENT NO. : 5,679,460
DATED : October 21, 1997
INVENTOR(S) : Josephus Maria Schakenraad et al.

It is certified that error appears in the above-identified patent and that said Letters Patent is hereby corrected as shown below:

Title Page, under "[75] Inventors," should read:
--Josephus Maria Schakenraad, Haren; Hendrik Jan Busscher, Thesinge; Ietse Stokroos, Gronigen, all of Netherlands--.

Figure 1D:
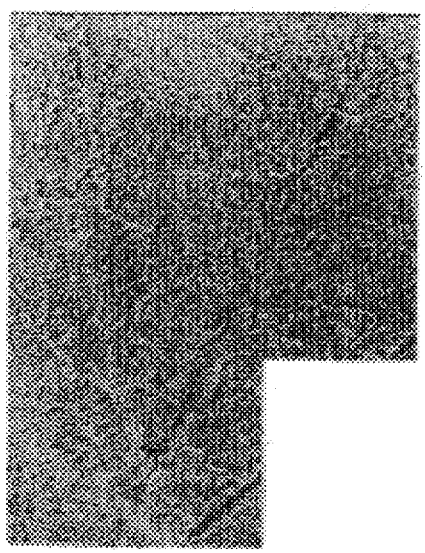
FIG. 1D is 10 min. ion-etching (8 mA/6 kV/$4\times10^{-5}$ torr argon pressure)
Figures 1, 1D:
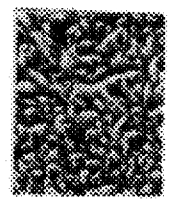
Figure 1E:
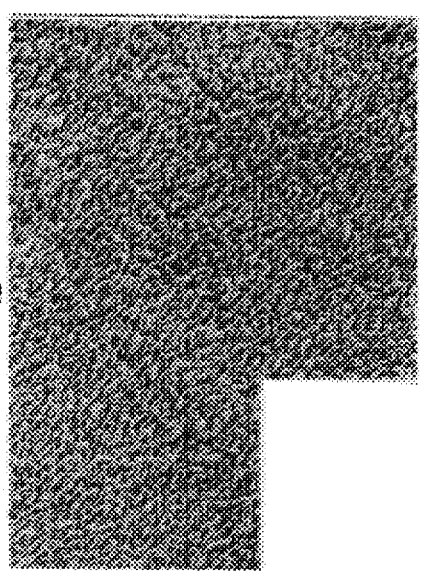
FIG. 1E is 30 min. ion-etching (8 mA/6 kV/$4\times10^{-4}$ torr argon pressure)
Figures 1, 1E:
Figure 1F:
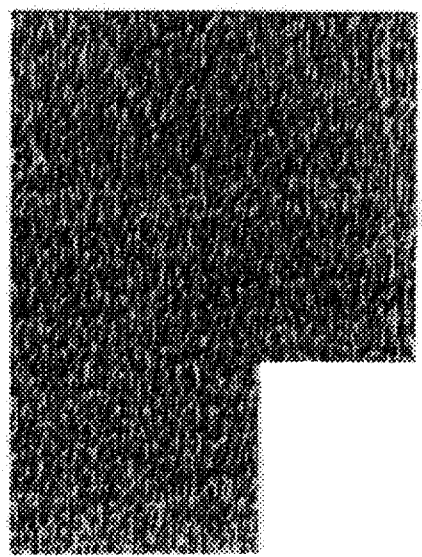
FIG. 1F is 60 min. ion-etching (8 mA/6 kV/$4\times10^{-4}$ torr argon pressure)
Figures 1, 1F:
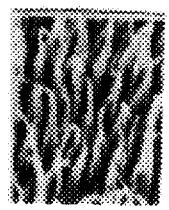
Figure 1G:
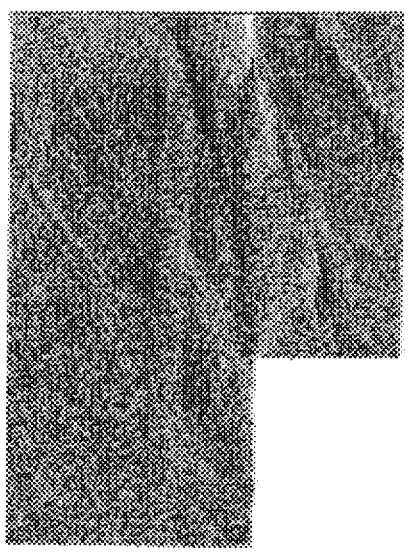
FIG. 1G is ion-etching according to D followed by glow discharging according to C
Figures 1, 1G:
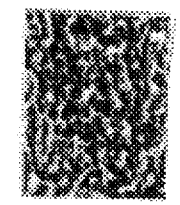
Figure 1H:
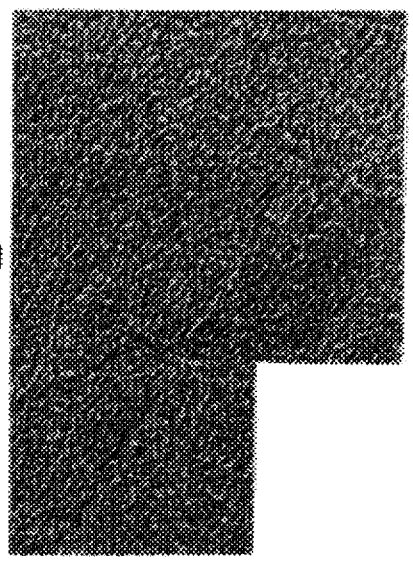
FIG. 1H is ion-etching according to E followed by glow discharging according to C
Figures 1, 1H:
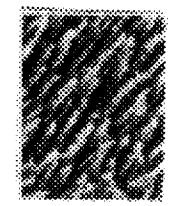
Figure 1I:
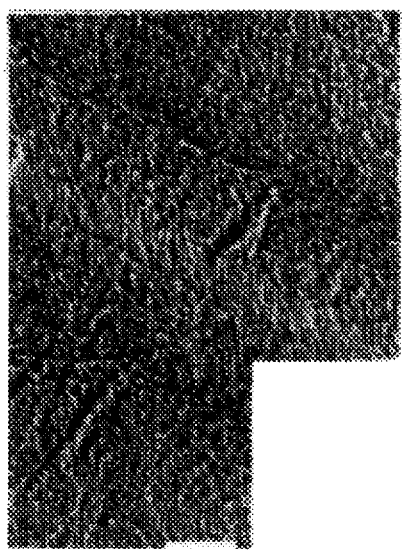
FIG. 1I is ion-etching according to F followed by glow discharging according to C (the bars show respectively 10 μm and 3 μm).
Figures 1, 1I:
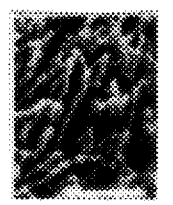

Column 3 Line 52, under FIG. 1D, "$4 \times 10^{-5}$" should read --$4 \times 10^{-4}$--.

Column 4 Line 12 "whole suffice" should read --whole surface--.

Column 4 Line 39 "$cm^2 33\ 10^4$" should read --$cm^2 \times 10^4$--.

Column 5 Line 42 Table 1, last column, next-to-last figure, "107 ± 20" should read "107 ± 10--.

Column 5 Line 44 "Hydrophobicly" should read --Hydrophilicly--.

Signed and Sealed this

Twenty-second Day of December, 1998

Attest:

BRUCE LEHMAN

*Attesting Officer*  *Commissioner of Patents and Trademarks*

UNITED STATES PATENT AND TRADEMARK OFFICE
CERTIFICATE OF CORRECTION

PATENT NO. : 5,679,460
DATED : October 21, 1997
INVENTOR(S) : Josephus Maria Schakenraad et al.

It is certified that error appears in the above-identified patent and that said Letters Patent is hereby corrected as shown below:

Column 3 Line 3 "$1 \times 10^{-6}$ to" should read --$1 \times 10^{-6}$ to--.

Column 5 Line 42 Table 1, last column, next-to-last figure, "$107 \pm 20$" should read --$107 \pm 10$--.

Signed and Sealed this

Sixteenth Day of March, 1999

Attest:

Attesting Officer

Q. TODD DICKINSON

Acting Commissioner of Patents and Trademarks